United States Patent
Bidard-Michelot et al.

(10) Patent No.: US 11,401,497 B2
(45) Date of Patent: Aug. 2, 2022

(54) **METHOD FOR RESTORING SEXUAL REPRODUCTION IN THE FUNGUS *TRICHODERMA REESEI***

(71) Applicant: IFP Energies Nouvelles, Rueil Malmaison (FR)

(72) Inventors: Frédérique Bidard-Michelot, l'Etang la Ville (FR); Laetitia Chan Ho Tong, Bry sur Marne (FR)

(73) Assignee: IFP Energies Nouvelles, Rueil Malmaison (FR)

( * ) Notice: Subject to any disclaimer, the term of this patent is extended or adjusted under 35 U.S.C. 154(b) by 0 days.

(21) Appl. No.: 16/628,294

(22) PCT Filed: Jul. 9, 2018

(86) PCT No.: PCT/FR2018/051721
§ 371 (c)(1),
(2) Date: Jan. 3, 2020

(87) PCT Pub. No.: WO2019/008303
PCT Pub. Date: Jan. 10, 2019

(65) Prior Publication Data
US 2021/0009938 A1    Jan. 14, 2021

(30) Foreign Application Priority Data
Jul. 7, 2017    (FR) ..................... 1756469

(51) Int. Cl.
*C12N 1/14* (2006.01)
*C12N 9/42* (2006.01)

(52) U.S. Cl.
CPC ............. *C12N 1/14* (2013.01); *C12N 9/2437* (2013.01); *C12Y 302/01004* (2013.01)

(58) Field of Classification Search
CPC . C12N 1/14; C12N 9/2437; C12Y 302/01004
See application file for complete search history.

(56) References Cited

FOREIGN PATENT DOCUMENTS

| WO | 2014/102241 A1 | 7/2014 |
| WO | 2015/086701 A1 | 6/2015 |

OTHER PUBLICATIONS

C. Siebel et al. "ENVOY Is a Major Determinant in Regulation of Sexual Development in Hypocrea jecorina (*Trichoderma reesei*)", Eukayotic Cell 11(7):885-895 (Year: 2012).*
International Search Report issued in corresponding International Patent Application No. PCT/FR2018/051721 dated Sep. 14, 2018.
Seidl et al., "Sexual development in the industrial workhorse *Trichoderma reesei*," Proceedings of the National Academy of Sciences, 106: 113909-13914 (2009).
Linke et al., "Restoration of female fertility in *Trichoderma reesei* QM6a provides the basis for inbreeding in this industrial cellulase producing fungus," Biotechnology for Biofuels, 8: 155 (2015).
Benkhali et al., "A Network of HMG-box Transcription Factors Regulates Sexual Cycle in the Fungus Podospora anserina," PLOS Genetics, 9: e1003642 (2013).
Jamet-Vierny et al., "IDC1, a Pezizomycotina-specific gene that belongs to the PaMpk1 MAP kinase transduction cascade of the filamentous fungus Podospora anserina," Fungal Genetics and Biology, 44: 1219-1230 (2007).

* cited by examiner

*Primary Examiner* — Tekchand Saidha
(74) *Attorney, Agent, or Firm* — Morgan, Lewis & Bockius LLP

(57) ABSTRACT

The present invention relates to a method for restoring sexual reproduction between two sterile, female strains of *Trichoderma reesei* using a helper strain ΔMAT, said helper strain being a fertile female strain of *Trichoderma reesei* in which the sexual-type locus MAT has been eliminated.

18 Claims, 6 Drawing Sheets
Specification includes a Sequence Listing.

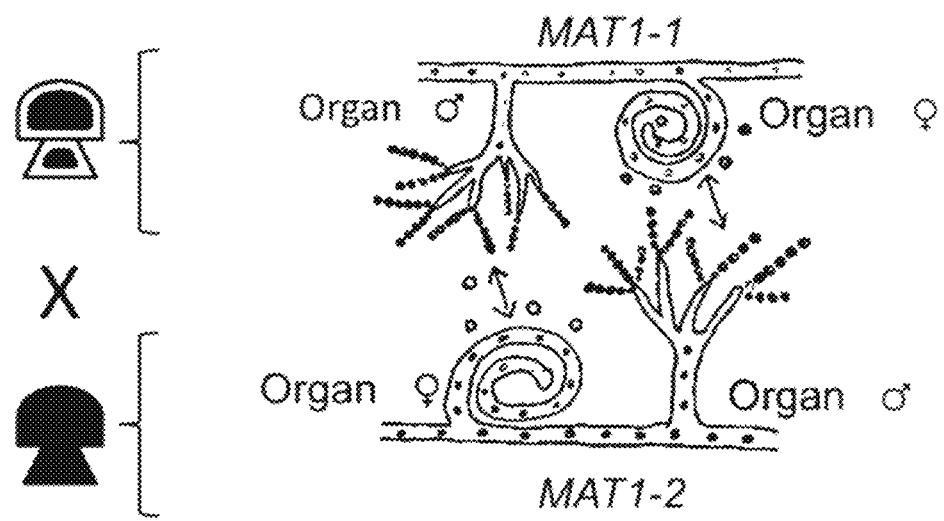
Figure 1: Principle of sexual reproduction in the filamentous fungus *T. reesei*

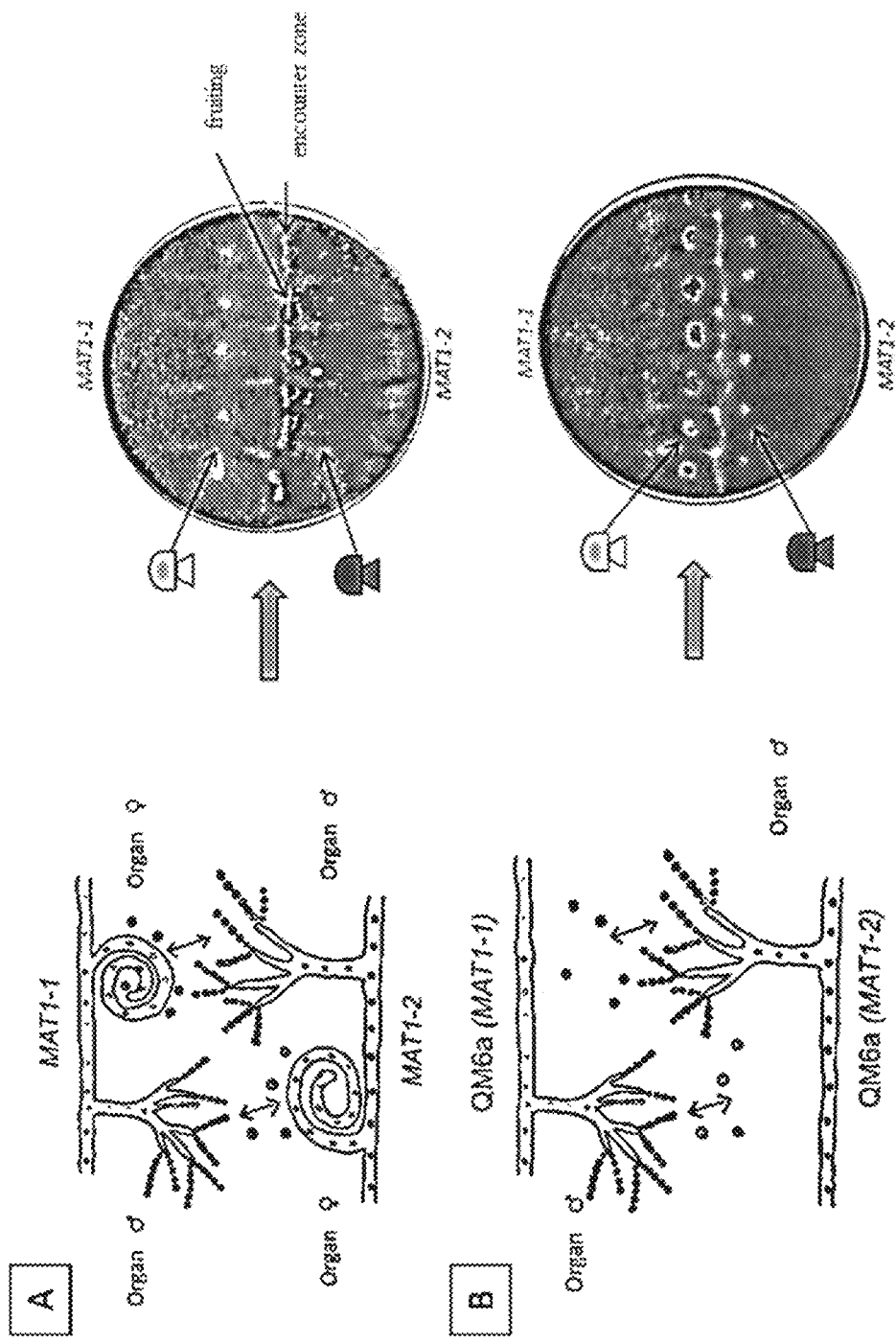
Figure 2: Sexual reproduction in *T. reesei*. Between two natural isolates (A) and between two QM6a strains (B)

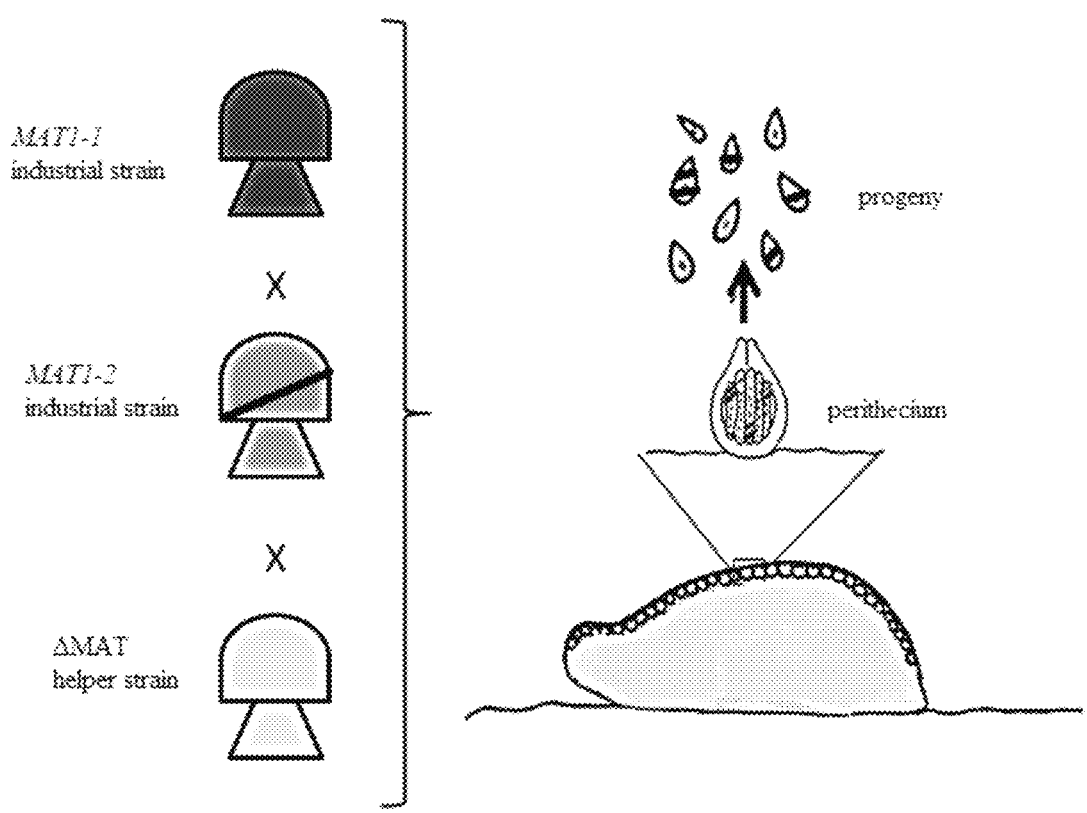
Figure 3: Principe of the method of the helper strain

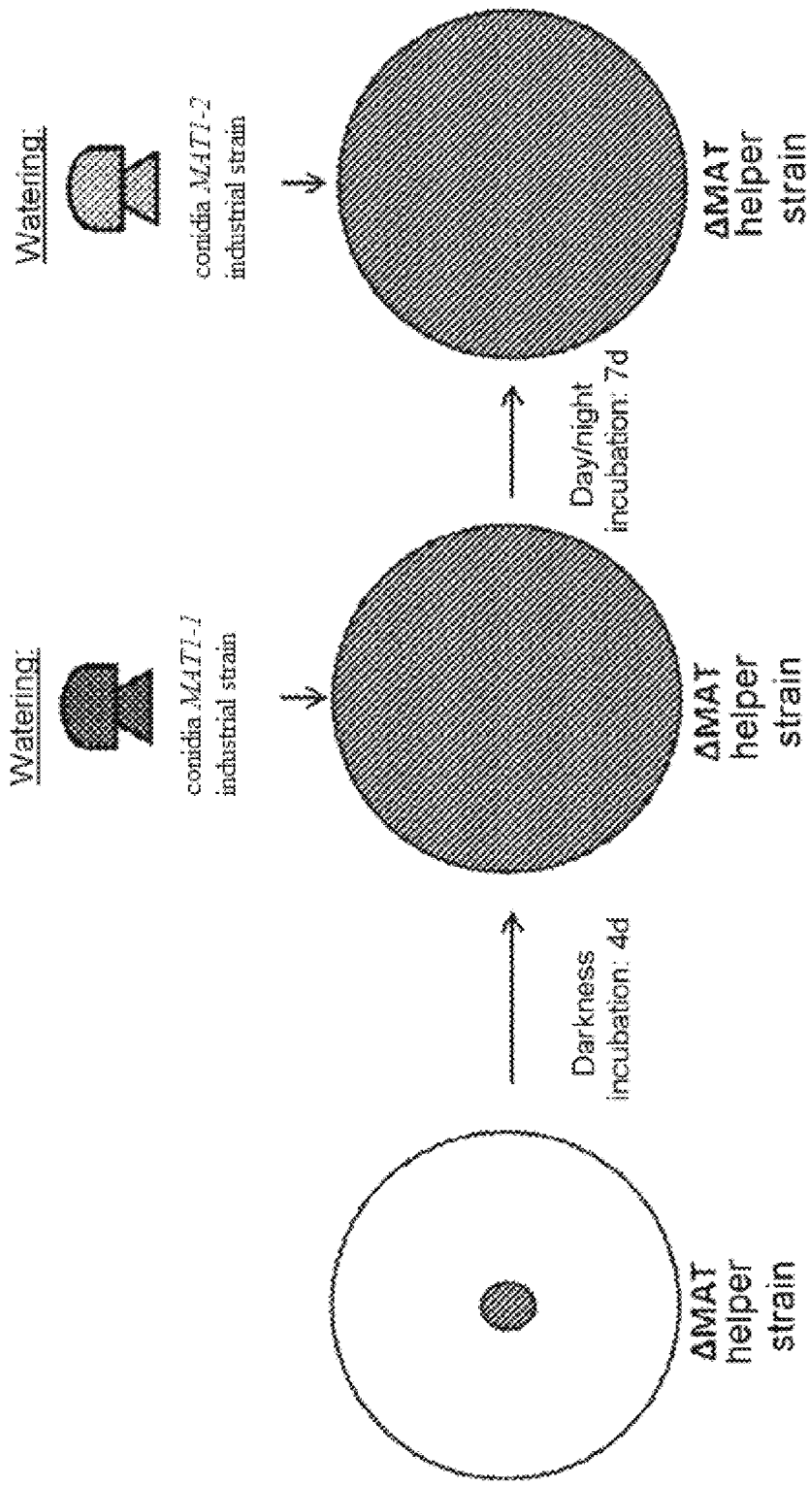
Figure 4: Protocol for implementing the method of the helper strain

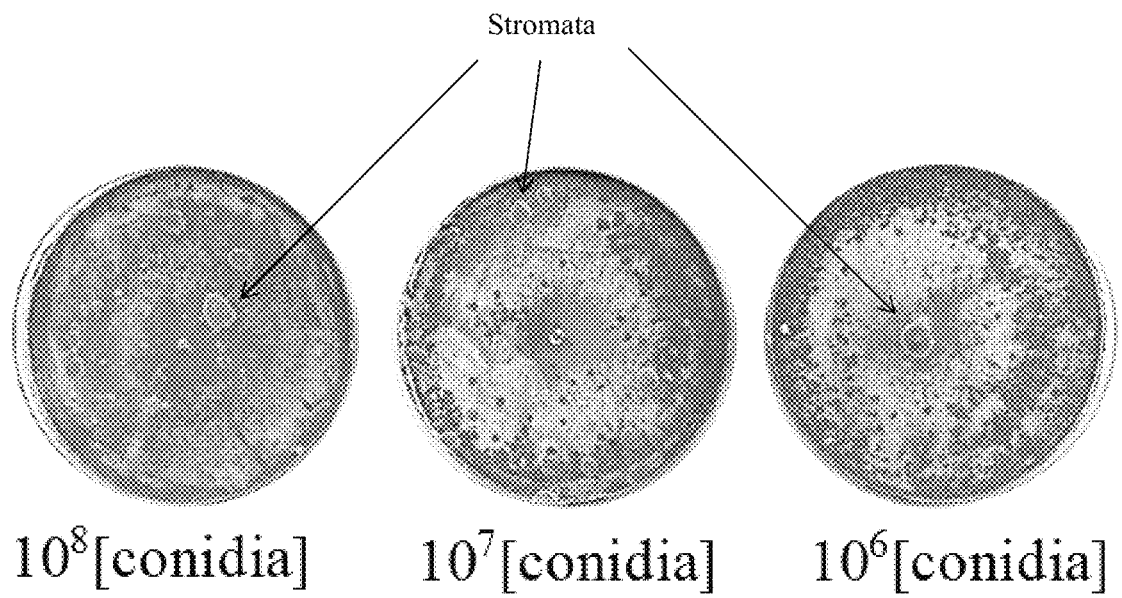
Figure 5: Stromata obtained following implementation of the method of the helper strain
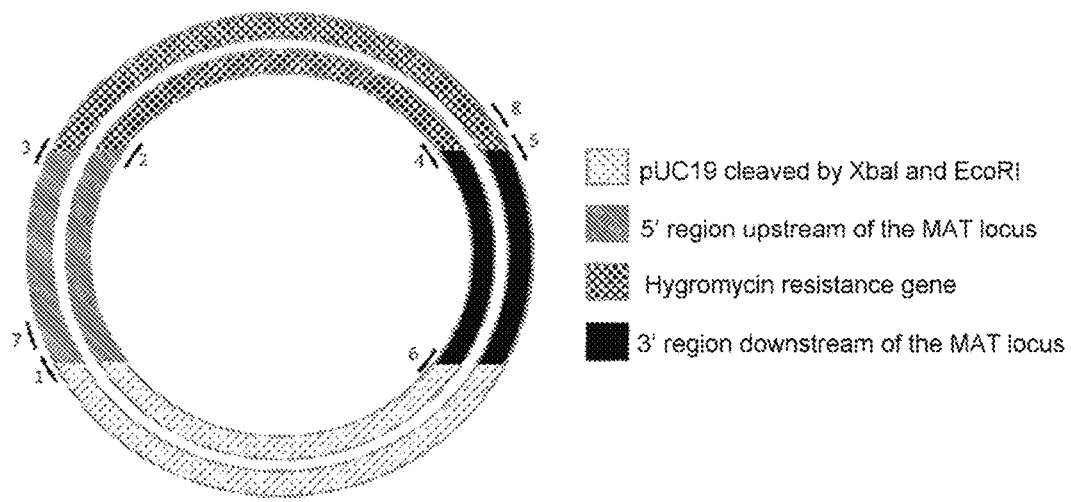
Figure 6: Final assembly of the knockout cassette in the pUC19 plasmid

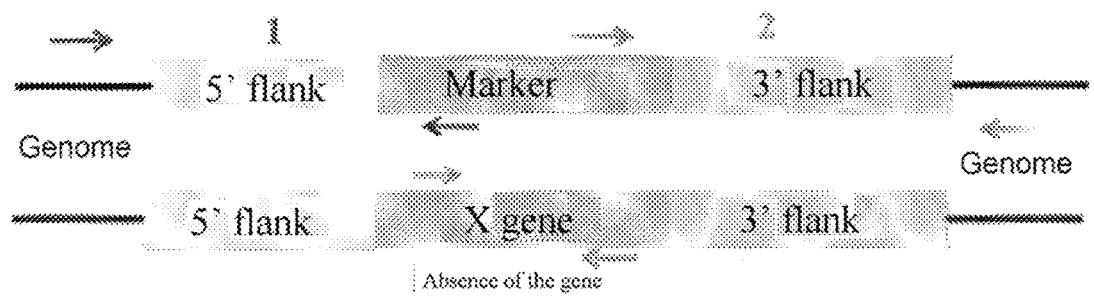
Figure 7 : Position of the primers chosen for the amplification of the various fragments of the knockout cassette
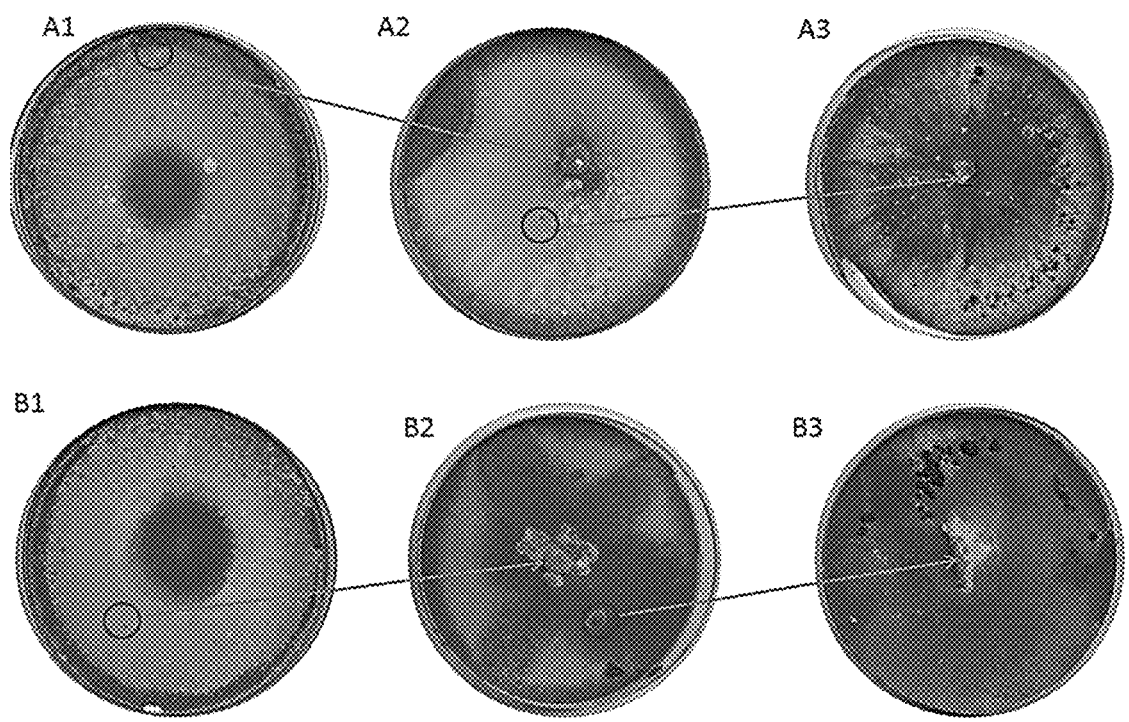
Figure 8 : Amplification of stromata

SEQUENCE LISTING

```
<160> NUMBER OF SEQ ID NOS: 17

<210> SEQ ID NO 1
<211> LENGTH: 45
<212> TYPE: DNA
<213> ORGANISM: Artificial sequence
<220> FEATURE:
<223> OTHER INFORMATION: Primer

<400> SEQUENCE: 1
tgcatgcctg caggtcgact ctagaccctt cctgaccctg gactg                45

<210> SEQ ID NO 2
<211> LENGTH: 30
<212> TYPE: DNA
<213> ORGANISM: Artificial sequence
<220> FEATURE:
<223> OTHER INFORMATION: Primer

<400> SEQUENCE: 2
ggtacacttg gactgcgttg actgatggtg                                 30

<210> SEQ ID NO 3
<211> LENGTH: 31
<212> TYPE: DNA
<213> ORGANISM: Artificial sequence
<220> FEATURE:
<223> OTHER INFORMATION: Primer

<400> SEQUENCE: 3
caacgcagtc caagtgtacc tgtgcattct g                               31

<210> SEQ ID NO 4
<211> LENGTH: 30
<212> TYPE: DNA
<213> ORGANISM: Artificial sequence
<220> FEATURE:
<223> OTHER INFORMATION: Primer

<400> SEQUENCE: 4
cctttgccaa ggcagtgcta gtgtgtgtac                                 30

<210> SEQ ID NO 5
```

```
<211> LENGTH: 31
<212> TYPE: DNA
<213> ORGANISM: Artificial sequence
<220> FEATURE:
<223> OTHER INFORMATION: Primer

<400> SEQUENCE: 5
tagcactgcc ttggcaaagg ctagacacta c                              31

<210> SEQ ID NO 6
<211> LENGTH: 45
<212> TYPE: DNA
<213> ORGANISM: Artificial sequence
<220> FEATURE:
<223> OTHER INFORMATION: Primer

<400> SEQUENCE: 6
ttgtaaaacg acggccagtg aattcatgta caattaccac atgcg               45

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ccagggcttt gagagcagta                                           20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ctggtggctg acacttgcta                                           20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gtactggttg ttgggctgtg                                           20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
cggagcaact ctcaggaaac                                           20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
```

```
ctccgtaaca cccaatacgc                                              20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ctctgggcaa agcaccaatc                                              20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
ttcagtgttg gccattttga                                              20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
gcttctcaag caaggcaagt                                              20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
atgggtaagg aggacaagac                                              20

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
ggaagtacca gtgatcatgt t                                            21

<210> SEQ ID NO 17
<211> LENGTH: 7933
<212> TYPE: DNA
<213> ORGANISM: Artificial sequence
<220> FEATURE:
<223> OTHER INFORMATION: Primer

<400> SEQUENCE: 17
tgcagcactg gggccagatg gtaagccctc ccgtatcgta gttatctaca cgacggggag     60
tcaggcaact atgatgaac gaaatagaca gatcgctgag ataggtgcct cactgattaa    120
gcattggtaa ctgtcagacc aagtttactc atatatactt tagattgatt taaaacttca   180
```

```
tttttaattt aaaaggatct aggtgaagat ccttttttgat aatctcatga ccaaaatccc    240
ttaacgtgag ttttcgttcc actgagcgtc agacccgta gaaaagatca aaggatcttc     300
ttgagatcct ttttttctgc gcgtaatctg ctgcttgcaa acaaaaaaac caccgctacc    360
agcggtggtt tgtttgccgg atcaagagct accaactctt tttccgaagg taactggctt    420
cagcagagcg cagataccaa atactgttct tctagtgtag ccgtagttag gccaccactt    480
caagaactct gtagcaccgc ctacatacct cgctctgcta atcctgttac cagtggctgc    540
tgccagtggc gataagtcgt gtcttaccgg gttggactca agacgatagt taccggataa    600
ggcgcagcgg tcgggctgaa cggggggttc gtgcacacag cccagcttgg agcgaacgac    660
ctacaccgaa ctgagatacc tacagcgtga gctatgagaa agcgccacgc ttcccgaagg    720
gagaaaggcg gacaggtatc cggtaagcgg cagggtcgga acaggagagc gcacgaggga    780
gcttccaggg ggaaacgcct ggtatcttta tagtcctgtc gggtttcgcc acctctgact    840
tgagcgtcga ttttgtgat gctcgtcagg ggggcggagc ctatgaaaa acgccagcaa    900 cgcggccttt ttacggttcc tggccttttg ctggccttt gctcacatgt tctttcctgc    960
gttatcccct gattctgtgg ataaccgtat taccgccttt gagtgagctg ataccgctcg    1020
ccgcagccga acgaccgagc gcagcgagtc agtgagcgag gaagcggaag agcgcccaat    1080
acgcaaaccg cctctccccg cgcgttggcc gattcattaa tgcagctggc acgacaggtt    1140
tcccgactgg aaagcgggca gtgagcgcaa cgcaattaat gtgagttagc tcactcatta    1200
ggcaccccag gctttacact ttatgcttcc ggctcgtatg ttgtgtggaa ttgtgagcgg    1260
ataacaattt cacacaggaa acagctatga ccatgattac gccaagcttg catgcctgca    1320
ggtcgactct agaccccttcc tgaccctgga ctgtccagtg gccaccgggg cgtggctcca    1380
gggctttgag agcagtaatt ggtgggagtt tggtagttga catggctgcg aaaattggtg    1440
tccttcagaa gttggtcaag gttgattatt gaatcagttt gcttcgagtg gtgatgaaga    1500
aatccccaga gtatgagggt atgggatcag tgggatgttg aaggtgagaa taacaggtct    1560
gcgaaggggc cgccgagtcc gtgtggggtc ttcttcaggt tgctaaggtt ctactctctg    1620
caagtgaaat aaaagtgaag gatcgagtg aatggacgct tgtgcccatg agttcacctc    1680
acttttaact cactctgctg catctgagac cctgcagaag taaggcgaaa gcttgtcagt    1740
gggaaaagac ccacggcacc atttaaatgt ttacgtatgt ggatatccgc taaatacgcc    1800
tgctgtttgt gttggctctt gccaagatca atttcagctt ctgccagtat ttcaagtcaa    1860
acgttgtcat gaactacctc catgttgaaa ttcttcatgg atcgtacact gtccgtttgg    1920
aatctcagat ctgaatcgta tgaaataaca gaatcgagct ttcgcaacta gatgtcccag    1980
caacattgcg cccctggaaa gtgataaact gcaactgcat ttgtgtgaaa ccattggcat    2040
aagtgattgc gctctctggc ggaacggacg aagacatgtt gcttgatctt atcctttcca    2100
tggagatcgt atatattctg atttgatgca aatggtatgt acataaatgt ccttcacgaa    2160
ctttcaggtt gttcccaaag ctaaacttca cgcgcatctt gggtgaagta ctgcctcgaa    2220
cgtcatgcac acctggagag cattttgctg gtgtgcgaaa tgaggatatc tccacggtgg    2280
gcgtattgtt acgaagatgc acaccctctg gcgatgggcg ggtgggactg ctagattcta    2340
gccccaacac ttcctttaga aggtacctag gtacgcttgc aaggttcctt aggaggtagc    2400
ttgtcgttgg caagcagaaa tacatattac ctagtagtac ctaggtttct accttacctt    2460
cttacatatc agtagtacct agtcattttt ccccaaggag ggagggtgag aaaagagaga    2520
taggtgggga gcgcgcactg acctggcgct aaataacgga ggggctgggg gggcactatt    2580
```

```
cagattcact cgctttgggt tggcagctct catcaataaa ggccagtaag ttgaatcacc    2640
acggcacgtt ccggctcact tgtagctcac cctccaccca cagccttttc aattcttcaa    2700
agcattacct aggcgaccga aaacttccta cctctcaagt tcctcctatc ttccaactcc    2760
tgcatcaacg ttcatatccc atcttctcgc gatatattac cagagcaagc ccgcaccatc    2820
agtcaacgca gtccaagtgt acctgtgcat tctgggtaaa cgactcatag gagagttgta    2880
aaaaagtttc ggccggcgta ttgggtgtta cggagcattc actaggcaac catgcatcct    2940
tactattgta taccatctta gtaggaatga tttcgaggtt tatacctacg atgaatgtgt    3000
gtcctgtagg cttgagagtt caaggaagaa acatgcaatt atctttgcga acccagggct    3060
ggtgacggaa ttttcatagt caagctatca gagtaaagaa gaggagcatg tcaaagtaca    3120
attagagaca aatatatagt cgcgtggagc caagagcgga ttcctcagtc tcgtaggtct    3180
cttgacgacc gttgatctgc ttgatctcgt ctcccgaaaa tgaaaatagc tctgctaagc    3240
tattcttctc ttcgccggag cctgaaggcg ttactaggtt gcagtcaatg cattaatgca    3300
ttgcagatga gctgtatctg gaagaggtaa acccgaaaac gcgttttatt cttgttgaca    3360
tggagctatt aaatcactag aaggcactct ttgctgcttg gacaaatgaa cgtatcttat    3420
cgagatcctg aacaccattt gtctcaactc cggctagcga attctcgact cattcctttg    3480
ccctcggacg agtgctgggg cgtcggtttc cactatcggc gagtacttct acacagccat    3540
cggtccagac ggccgcgctt ctgcgggcga tttgtgtacg cccgacagtc ccggctccgg    3600
atcggacgat tgcgtcgcat cgaccctgcg cccaagctgc atcatcgaaa ttgccgtcaa    3660
ccaagctctg atagagttgg tcaagaccaa tgcggagcat atacgcccgg agtcgtggcg    3720
atcctgcaag ctccggatgc ctccgctcga agtagcgcgt ctgctgctcc atacaagcca    3780
accacggcct ccagaagaag atgttggcga cctcgtattg gaatccccg aacatcgcct    3840 cgctccagtc aatgaccgct gttatgcggc cattgtccgt caggacattg ttggagccga    3900
aatccgcgtg cacgaggtgc cggacttcgg ggcagtcctc ggcccaaagc atcagctcat    3960
cgagagcctg cgcgacggac gcactgacgg tgtcgtccat cacagtttgc cagtgataca    4020 catgggatc agcaatcgcg catatgaaat cacgccatgt agtgtattga ccgattcctt    4080
gcggtccgaa tgggccgaac ccgctcgtct ggctaagatc ggccgcagcg atcgcatcca    4140
tagcctccgc gaccggttgt agaacagcgg gcagttcgg ttcaggcagg tcttgcaacg    4200
tgacaccctg tgcacggcgg gagatgcaat aggtcaggct ctcgctaaac tccccaatgt    4260
caagcacttc cggaatcggg agcgcggccg atgcaaagtg ccgataaaca taacgatctt    4320
tgtagaaacc atcggcgcag ctatttaccc gcaggacata tccacgccct cctacatcga    4380
agctgaaagc acgagattct tcgccctccg agagctgcat caggtcggag acgctgtcga    4440 actttttcgat cagaaacttc tcgacagacg tcgcggtgag ttcaggcttt ttcatgatgg    4500
ccctcctacc ggtgatctca gctgtaggaa agagaagaag gttagtagtc gacatggtgg    4560
ccctcctata gtgagtcgta ttatactatg ccgatatact atgccgatga ttaattgtca    4620
acactaggcg ccggtcacaa ctagtagata tcacttacgt gttgagaggc ggcatgcgat    4680
aagaggtgta attcctgag aacatcttgt tgccctgctt tccgtgcgaa atactaccgg    4740
tactttgggg aaacaaggga acaggagggc gctgctgtgc gcggttctga gtgttcagga    4800
ttgaagctga agaaggtgct gaggaagcgt agaactgttg cggacgcgag ttctgagaag    4860
agctgtaccg attggtgaaa gccgaagaag tgagttggtg ccctgttgcc tggataatgt    4920
```

-continued

```
ttgcaactcg ctggttctgc agagacggag acaaatgctg gctacgatgt tgctgattca    4980
ggttgatacc tcggtcgaga cactgttttg gtttgatagg gtggatttgg ttgcagagaa    5040
gagaaaggaa ggtcaaagag ggaaaactgg gcggagggaa ggattttgta tcaggcagca    5100
aactgccact gcagtggccc tggcagtgcc gggcgaggca cccacgcacg gccgcgcaac    5160
cggttggtcc ttgcccacca cgaaacccct ctgaaaggtc agatggaagt gtgcgacagt    5220
gcgcgtcccc aagccaatgc aggcgccatg cactccccac ccgcaagatt cactgtgcgt    5280
tcttattggt tgccgcaagg ccagccaaag ggggaagtat gagtcacagc accgatacaa    5340
gaaaattgca gaactaacat atggatgcgc gcgctattct gtagagctct ggcaaagca    5400
ccaatcctgc gggtcggtac acacactagc actgccttgg caaaggctag acactacgga    5460
aatctcgctt cggtccttat agattctgtg agatattgtc gcttgtgcca atggtaaggc    5520
cgaaatgatg cttttaatgg aacagctcat ctaacaggcc acagatgatt tcatagctag    5580
gctgaatgcc tcgggcagtt tcgggcatgg tacaaacaga gtaccacgtc cctaaaacag    5640
gcggaacttt caccgctcag tttcctcgac agctttcaga ggtttgtaag tgcaccttgc    5700
tatctatttc tctggacggc acagtaactg atcattgtta catgaacagt agttcttgcc    5760
ttggtggacg aggaaacaga ccacttcata ggaaatcttt ttggaacgac ctgcagagat    5820
gtgcaactac acaccgagtt acccagacta caagttcagg gccatggagc cttgggcgga    5880
gactacctaa tatcagagag caagctgtgg ctgcctctac accgggtcaa gcattggaat    5940
caggctgtgt ttttcaagat agcgagagct ttggttgtaa tagggttcca tcagcatact    6000
atgccgattg cctagtaggc actcataacc gtggcaacca agccggacac aggtccttct    6060
agatcacagt tccatattct tcgagatgat aaattaaagt caaatgctac catctacaac    6120
ctccaatctg caactttgct tctctttcac actagacctc tcgcctcccg tcactctgcc    6180
aatgatgaac actagcatct cgtatatcgt gaaaggttta gctaccctca aacttgagtt    6240
gtggagatca actgatctcg ttcggactac attgcggcga caacttgaat tggacacgat    6300
aaggaaaagg ccaaactttg tgaggtgctg agggcagtaa gcacgacagt ctaaagagaa    6360
agaaatgccg cgttcactac agccatttga ggtctaacaa caagctgatt caactgcaac    6420
aggcgctatg tcaagaaggt gatccgttcc aatcgctgct ccaaatgaaa gtaccgcacc    6480
gccactcaga gcctcgttct ttctcgccgg agggacctag cggccgggcg cagatataga    6540
acgaccttcc tgttagcaag tgtcagccac cagctggtct gcgcatgtgg taattgtaca    6600
tgaattcact ggccgtcgtt ttacaacgtc gtgactggga aaaccctggc gttacccaac    6660
ttaatcgcct tgcagcacat ccccctttcg ccagctggcg taatagcgaa gaggcccgca    6720
ccgatcgccc ttcccaacag ttgcgcagcc tgaatggcga atggcgcctg atgcggtatt    6780
ttctccttac gcatctgtgc ggtatttcac accgcatatg gtgcactctc agtacaatct    6840
gctctgatgc cgcatagtta agccagcccc gacacccgcc aacacccgct gacgcgccct    6900
gacgggcttg tctgctcccg gcatccgctt acagacaagc tgtgaccgtc tccgggagct    6960
gcatgtgtca gaggttttca ccgtcatcac cgaaacgcgc gagacgaaag ggcctcgtga    7020
tacgcctatt tttataggtt aatgtcatga taataatggt tcttagacg tcaggtggca    7080
cttttcgggg aaatgtgcgc ggaacccta tttgtttatt tttctaaata cattcaaata    7140
tgtatccgct catgagacaa taaccctgat aaatgcttca ataatattga aaaggaaga    7200
gtatgagtat tcaacatttc cgtgtcgccc ttattccctt ttttgcggca ttttgccttc    7260
ctgttttgc tcacccagaa acgctggtga agtaaaaga tgctgaagat cagttgggtg    7320
```

```
cacgagtggg ttacatcgaa ctggatctca acagcggtaa gatccttgag agttttcgcc    7380
ccgaagaacg ttttccaatg atgagcactt ttaaagttct gctatgtggc gcggtattat    7440
cccgtattga cgccgggcaa gagcaactcg gtcgccgcat acactattct cagaatgact    7500
tggttgagta ctcaccagtc acagaaaagc atcttacgga tggcatgaca gtaagagaat    7560
tatgcagtgc tgccataacc atgagtgata acactgcggc caacttactt ctgacaacga    7620
tcggaggacc gaaggagcta accgcttttt tgcacaacat gggggatcat gtaactcgcc    7680
ttgatcgttg ggaaccggag ctgaatgaag ccataccaaa cgacgagcgt gacaccacga    7740
tgcctgtagc aatggcaaca acgttgcgca aactattaac tggcgaacta cttactctag    7800
cttcccggca acaattaata gactggatgg aggcggataa agttgcagga ccacttctgc    7860
gctcggccct tccggctggc tggtttattg ctgataaatc tggagccggt gagcgtgggt    7920
ctcgcggtat cat                                                      7933
```

METHOD FOR RESTORING SEXUAL REPRODUCTION IN THE FUNGUS *TRICHODERMA REESEI*

SEQUENCE LISTING SUBMISSION VIA EFS-WEB

A computer readable text file, entitled "SequenceListing.txt," created on or about Apr. 9, 2020 with a file size of about 14 kb contains the sequence listing for this application and is hereby incorporated by reference in its entirety.

The present invention relates to a method for restoring sexual reproduction between two sterile female strains of the fungus *Trichoderma reesei*.

*Trichoderma reesei* (*T. reesei*) is a species of cellulolytic filamentous fungus, of the *Trichoderma* genus, which was discovered during the Second World War in the South Pacific. This fungus has the capacity to secrete a large amount of cellulosic enzymes (cellulases and hemicellulases), and is at the current time mainly used in the second-generation biofuel production cycle. Indeed, the enzymes produced by this fungus are particularly useful for converting plant biomass matter into bioproducts that are industrially useful, such as bioethanol.

Second-generation biofuels (derived from non-food resources) are particularly of interest at the current time, given that the first-generation biofuels (derived from food resources) can only be produced in limited amount, since they compete with food production.

The method for producing second-generation biofuels comprises four main steps: pretreatment of the lignocellulosic biomass, enzymatic hydrolysis of the lignocellulosic biomass, fermentation and distillation.

Even though all the steps of second-generation biofuel production can and must be optimized—in order to increase production—, the enzymatic hydrolysis step is given particular emphasis. This hydrolysis step involves cellulase-type enzymes produced by the filamentous fungus *T. reesei*.

More generally, *Trichoderma reesei* could be used as a platform strain for the production of homologous or heterologous proteins of industrial interest. In order to optimize the performance qualities of *Trichoderma reesei*, it is essential to improve the strains of *Trichoderma reesei* which produced the proteins of interest.

Among the methods of improvement envisioned for decreasing the costs of the hydrolysis, genetic engineering of *T. reesei* is thus a solution. It makes it possible to improve the secretion performance qualities of the cellulase-producing filamentous fungus, and the properties of the enzymes, and to control the stability of the strains under industrial conditions.

Mutagenesis is a technique commonly used in gene therapy. It aims to intentionally introduce mutations into the DNA in order to create genetically modified genes. This can make it possible to generate strains with characteristics that are advantageous from an industrial point of view. There are two mutagenesis methods commonly used for introducing mutations into *T. reesei*: random mutagenesis and site-directed mutagenesis.

Random mutagenesis consists in inducing non-targeted mutations, anywhere in the DNA. These mutations are caused by exposure of the target organism to mutagenic chemical agents or to radiation. Given that mutations are a natural phenomenon, random mutagenesis is thus considered to be an accelerator of this natural process and the resulting organisms are considered to be natural and not to be genetically modified organisms (GMOs); they are thus not subject to the obligation of traceability. However, this method causes, in addition to the mutation responsible for the character of interest, a large number of undesirable mutations, termed "collateral" mutations, which contribute, by accumulating, to the instability, to the poor health, or even to the death of the mutated organism.

Site-directed mutagenesis makes it possible to introduce identified mutations into a precise gene. To do this, the DNA of interest containing the mutations is synthesized and then introduced into the cell to be mutated where the DNA repair mechanism takes care of integrating it into the genome. The use of a selectable marker makes it possible to identify the cells that have integrated the mutation with respect to those which have not integrated it. However, the organisms which have undergone this mutagenesis are considered to be GMOs (because of the introduction of exogenous DNA), and are thus subject to an obligation of traceability.

In the case of the use of *T. reesei* for the production of second-generation biofuels, the improvement in the hydrolysis step, via the introduction of mutations (random or site-directed) into *T. reesei*, is thus not satisfactory, because of the accumulation of the undesirable mutations that this brings about, or else because of the introduction of exogenous DNA. There is thus a need for a new method of improving the hydrolysis step.

The inventors of the present invention have thus developed a new method for improving the performance qualities of *T. reesei* using the sexual reproduction of *T. reesei*. At the current time, the sexual reproduction of *T. reesei* has never been used as a tool for improvement since *T. reesei* has always been considered to be unable to perform sexual reproduction. Nevertheless, the discovery of a sexuality in *T. reesei* (Seidl et al., 2009) has opened up new possibilities for genetic improvement of the strains. Sexual reproduction makes it possible, inter alia, to create genetic diversity, to conserve beneficial mutations and to delete the "collateral" mutations from the genome.

*T. reesei* is a fungus termed heterothallic, that is to say that sexual reproduction is possible only between individuals of compatible mating type (MAT1-1 and MAT1-2). Furthermore, *T. reesei* is hermaphrodite, that is to say that a strain produces both male and female sex organs (FIG. 1).

Sexual reproduction between two fertile and compatible natural isolates of *T. reesei* gives rise to stromata which contain the progeny (FIG. 2A).

In order to test sexual reproduction on industrial strains, a strain QM6a MAT1-1 was constructed by genetic engineering (Seidl et al., 2009). Sexual reproduction between the compatible QM6a strains does not make it possible to obtain stromata since these strains are sterile female strains (FIG. 2B) (Seidl et al., 2009).

All the known existing industrial strains of *T. reesei* were generated from the natural strain QM6a. Given that the natural strain QM6a is of MAT1-2 mating type, all the industrial strains of *T. reesei* are at the current time of MAT1-2 mating type, and are sterile female, but fertile male.

Sexual reproduction may be a rapid and effective tool for improvement, but if it cannot take place between the industrial strains, its usefulness remains limited. Scientific studies have attempted to understand why the industrial strains of *T. reesei* are sterile female and how to remedy this. These research studies have made it possible to identify the idc1 gene as determining female sterility and show that replacing the defective gene with a functioning gene makes it possible to re-establish female fertility of the QM6a strain and to carry out sexual reproduction (Kubicek et al., 2014 (WO2014/102241); Linke et al., 2015).

Nevertheless, this strategy has a major drawback. Indeed, it requires introducing the functional gene into each of the industrial strains to be reproduced in order to be able to restore female fertility in the industrial strains. Secondly, this strategy does not take into account the fact that the industrial strains are derived from successive mutagenesis and that it is possible that other genes that are important for female fertility have been modified. Thus, provision of the functional idc1 gene will not be sufficient to restore female fertility and thus to restore sexual reproduction between two sterile female strains of *T. reesei*. Thus, being capable of restoring female fertility in the QM6a strain does not mean that it will be possible for it to be restored in the industrial strains generated from said QM6a strain.

There is thus a need for a method which makes it possible to restore sexual reproduction between two sterile female strains of *T. reesei*, in particular the QM6a strain or the sterile female industrial strains derived from the QM6a strain or any other sterile female strain of *T. reesei*.

The inventors of the present invention have thus developed a strategy for restoring sexual reproduction between two sterile female strains of *T. reesei* which requires neither the introduction into the sterile female strains of a functional version of the idc1 gene, which does not require verification of whether or not the presence of a functional version of the idc1 gene is sufficient to restore sexual reproduction, nor even the necessity of identifying and replacing the other genes which might be defective. The inventors of the present invention have thus developed a strategy for restoring sexual reproduction between two sterile female strains of *T. reesei* which is simple and efficient to put in place.

The present invention is in fact based on the results of the inventors according to which the use of a ΔMAT helper strain (that is to say a fertile female strain of *T. reesei* in which the mating-type locus, either MAT1-1 or MAT1-2, has been knocked out) in combination with sequential watering of the conidia of a sterile female strain of *T. reesei* of a first mating type, then of the conidia of a sterile female strain of *T. reesei* of a second mating type make it possible to restore sexual reproduction between these two sterile female strains.

The use of a helper strain has already been employed, but not in the species *T. reesei* (Silar, P. (2014)). More specifically, Jamet-Vierny et al. have described the use of a helper strain which makes it possible to provide the IDC1 proteins required for development of the stromata in the context of the reproduction of *Podospora anserina* strains. This method, which is based on the trikaryon production, makes it possible to restore the fertility of the *Podospora anserina* strains. However, it should be noted that this method cannot be used with the *T. reesei* strains: this is because the sole use of the trikaryon method does not make it possible to restore sexual reproduction between two sterile female strains of *T. reesei* (cf. example 2a).

The inventors of the present invention have nevertheless shown, surprisingly, that the trikaryon method makes it possible to restore sexual reproduction between two sterile female strains of *T. reesei* when it is used in combination with the sequential watering technique (that is to say watering with conidia of a sterile female strain of *T. reesei* of a first mating type, then conidia of a sterile female strain of *T. reesei* of a second mating type). This sequential watering, used in combination with a ΔMAT helper strain, makes it possible to restore sexual reproduction between two sterile female strains of *T. reesei*, and makes it possible to repeatedly obtain stromata (cf. example 2i).

In a first aspect, the invention thus relates to a method for restoring sexual reproduction between two sterile female strains of *Trichoderma reesei*, comprising the following steps:
  incubation in a suitable medium of a ΔMAT helper strain, said strain being a fertile female strain of *Trichoderma reesei* wherein the locus of the MAT mating type has been knocked out,
  a first watering of said ΔMAT helper strain with conidia of a first *Trichoderma reesei* strain of a first mating type,
  a second watering of said ΔMAT helper strain and of the conidia of a first *Trichoderma reesei* strain of a first mating type with conidia of a second *Trichoderma reesei* strain of a second mating type.

The "restoring sexual reproduction" according to the invention is understood to mean obtaining stromata from conidia of a first sterile female strain of *T. reesei* of a first mating type and of a second sterile female strain of *T. reesei* of a second mating type, by means of a ΔMAT strain.

A "sterile female strain of *T. reesei*" according to the invention is understood to mean all the *T. reesei* strains which are sterile female and fertile male. These are the *T. reesei* strains in which female fertility can be restored and which can be used in a method for restoring sexual reproduction according to the invention. Such strains are for example the strains QM6a, NG14, RUTC30, QM9414, CL847, QM9136, QM9978, QM9979, PC3-7, TU-6, etc. In other words, it involves all the strains produced from the QM6a strain and which are sterile female but these strains may also be *T. reesei* strains derived from other geographical isolates and which are sterile female and fertile male.

An "incubation in a suitable medium" according to the invention is understood to mean an incubation in a culture medium that is suitable for the growth of fungi. Such a medium is for example the PDA (Potato Dextrose Agar) medium, the SDA (Sabouraud Dextrose Agar) medium, the SPDA (Sweet Potato Dextrose Agar) medium, the MEA (Malt Extract Agar) medium, the Oatmeal Agar medium, the Cornmeal Agar medium, and is preferably a complete medium. A complete medium according to the invention is a medium which contains, in addition to the components of the minimum medium, the final metabolites which are required for growth, such as amino acids, vitamins, bases, etc., contrary to the minimum medium which is a medium comprising the chemical elements strictly required for the growth of an organism.

A "ΔMAT helper strain" according to the invention is understood to mean a *T. reesei* strain wherein the locus of the MAT1-1 or MAT1-2 mating-type has been knocked out. Said ΔMAT helper strain can be obtained by any of the gene-locus knockout techniques well known to those skilled in the art, or for example by the method described in example 1. The strain from which the ΔMAT helper strain is obtained must be fertile female. Although belonging to the *T. reesei* species, this helper strain does not fall within the definition of a "sterile female strain of *T. reesei*" according to the invention, because of the knockout of the locus of the MAT1-1 or MAT1-2 mating type. This helper strain is not involved in the karyogamy process since it has been subjected to a knockout of the locus of the mating type which regulates said process. The mechanism of the helper strain is unknown, but the hypotheses with regard to the way in which it works are the following:
  In the case of sexual reproduction between two sterile female strains: there may be fusion of the nuclei, but since the idc1 gene/IDC1 protein are defective, there is no hyphal recruitment for the construction and development of the stromata in which the karyogamy and the development of the progeny will take place.

In the case of reproduction between two sterile female strains and in the presence of the helper strain (FIG. 3): there may be fusion of the parental nuclei. In this case, there is expression of the idc1 gene by the helper strain, and thus synthesis of the IDC1 protein. Given that there is fusion of nuclei and the presence of the IDC1 proteins, there may be hyphal recruitment for the construction and development of the stromata in which the karyogamy and the development of the progeny will be able to take place. The female tissues are provided by the ΔMAT strain, while the zygotic tissues are provided by the sterile female strains.

The term "conidia" according to the invention is understood to mean a spore resulting from the vegetative multiplication of a fungus (such as *T. reesei*). The conidia of a *T. reesei* strain of the MAT1-1 mating type or of the MAT1-2 mating type are obtained according to the same conditions. For example, the conidia according to the invention of a first mating type or of a second mating type can be obtained by culturing and incubation in a suitable medium (such as PDA), respectively of a *T. reesei* strain of a first mating type or of a *T. reesei* strain of a second mating type, until the conidia appear. Preferably, the strains are incubated in light, and at a temperature of approximately 24-30° C. until the conidia appear. The conidia can then be recovered by rinsing the culture dish with distilled/sterile water. The term "conidia of a first *T. reesei* strain of a first mating type" according to the invention is understood to mean the conidia of one of the two *T. reesei* strains used in the method for restoring sexual reproduction according to the invention. The term "conidia of a second *T. reesei* strain of a second mating type" according to the invention is understood to mean the conidia of a *T. reesei* strain compatible with the first strain.

According to the invention, the mating type of the first *T. reesei* strain is MAT1-1 or MAT1-2, in particular MAT1-1.

According to the invention, the mating type of the second *T. reesei* strain is MAT1-1 or MAT1-2, in particular MAT1-2.

The terms "MAT1-1" or "MAT1-2" refer to the mating-type signs of the fungi. They are the two compatible mating types. Given that *T. reesei* is a fungus termed heterothallic, if the mating type of the first *T. reesei* strain is MAT1-1, then the mating type of the second *T. reesei* strain is necessarily MAT1-2. Conversely, if the mating type of the first *T. reesei* strain is MAT1-2, then the mating type of the second *T. reesei* strain is necessarily MAT1-1. In one preferred embodiment according to the invention, the mating type of the first *T. reesei* strain is MAT1-1, and the mating type of the second *T. reesei* strain is MAT1-2.

The first *T. reesei* strain and the second *T. reesei* strain that are used in a method for restoring sexual reproduction according to the invention may be identical or different strains, provided that the mating types are compatible. For example, when the strains are identical, the first strain may be a QM6a MAT1-1 strain and the second strain may be a QM6a MAT1-2 strain. Conversely, when the strains are different, the first strain may be an NG14 MAT1-1 strain and the second strain may be a RUTC30 MAT1-2 strain.

According to the invention, the *T. reesei* strain is any sterile female strain, such as the QM6a strain or a strain derived from the QM6a strain. Thus, in one embodiment of the invention, the first *T. reesei* strain is QM6a MAT1-1 or a derived strain, and the second *T. reesei* strain is QM6a MAT1-2 or a derived strain. In another embodiment of the invention, the first *T. reesei* strain is QM6a MAT1-2 or a derived strain, and the second *T. reesei* strain is QM6a MAT1-1 or a derived strain. In one preferred embodiment according to the invention, the *T. reesei* strain is QM6a MAT1-1 or a derived strain, and the second *T. reesei* strain is QM6a MAT1-2 or a derived strain. Preferably, the QM6a MAT1-2 strain refers to the strain deposited under the reference ATCC® 13613. A sterile female MAT1-1 strain (such as QM6a MAT1-1) can be obtained (i) by replacing the MAT1-2 locus with the MAT1-1 locus (for example according to the method described in the article Linke, R. et al. (2015)); (ii) by crossing (for example a QM6a MAT1-2 strain is crossed with a natural isolate of MAT1-1 mating type. Among the descendants obtained, the individuals of fertile female MAT1-1 mating type can be backcrossed with, for example, the QM6a MAT1-2 strain. This process is repeated at least seven times.

Systematically backcrossing the descendant with the QM6a MAT1-2 parent seven times in a row makes it possible to obtain a final descendant which has a genetic identity identical to that of the QM6a MAT1-2 strain with the exception of the mating type which will be MAT1-1. This is a backcross. The final descendant is of MAT1-1 mating type and is sterile female. An example of backcrossing is given in international application WO 2014/102241). However, at each step of these backcrosses, MAT1-1 or MAT1-2 sterile strains can be obtained and used in the method. The term "strain derived from the QM6a strain" according to the invention is understood to mean all the strains obtained from the QM6a natural isolate. This involves in particular all the industrial strains of *T. reesei* known at the current time or else all the sterile female *T. reesei* strains.

The term "watering" according to the invention is intended to mean pouring a solution containing the conidia of a first mating type (for example $10^7$ to $10^8$ MAT1-1 conidia) or pouring a solution containing the conidia of a second mating type (for example $10^7$ to $10^8$ MAT1-2 conidia). According to one preferred embodiment of the invention, the watering is only carried out with conidia of a first and/or second mating type (for example without the addition of cellular extract). Thus, in one preferred embodiment of the invention, the watering is carried out using a suitable solution containing only the conidia of a first and/or second mating type. A suitable solution is understood to mean for example water such as distilled water or sterile water.

According to one preferred embodiment of the invention, the incubation, of said ΔMAT helper strain, in a suitable medium is an incubation in the dark. The dark limits the production of conidia and promotes the access to the female sexual organs by the male sexual organs.

According to one preferred embodiment of the invention, the incubation, of said ΔMAT helper strain, in a suitable medium lasts at least 2 days, preferably between 2 and 6 days.

More particularly, according to one preferred embodiment of the invention, the incubation, of said ΔMAT helper strain, in a suitable medium lasts at least 4 days, preferably between 4 and 5 days. The incubation from 4 to 5 days makes it possible to optimize the restoring method (example 2i).

According to one embodiment of the invention, the conidia of the first *T. reesei* strain of a first mating type and/or the conidia of the second *T. reesei* strain of a second mating type are present at a concentration of at least $10^5$ conidia/ml.

More particularly, according to one preferred embodiment of the invention, the conidia of the first *T. reesei* strain of a first mating type and/or the conidia of the second *T. reesei* strain of a second mating type are present at a concentration of at least $10^6$ conidia/ml, in particular from $10^6$ to $10^8$ conidia/ml, and preferably from $10^7$ to $10^8$ conidia/ml. A concentration of $10^7$ to $10^8$ conidia/ml makes it possible to optimize the restoring method (cf. example 2i).

The optimal conditions for the sequential watering are an incubation (or preincubation) of the ΔMAT helper strain for 4 or 5 days, and also a concentration of conidia of $10^7$ to $10^8$ conidia/ml (cf. example 2i).

According to one preferred embodiment of the invention, the incubation, of said ΔMAT helper strain, in a suitable medium is carried out at an ambient temperature, in particular at 24° C.

According to one preferred embodiment of the invention, said method for restoring sexual reproduction between two sterile female strains of *T. reesei* comprises, in addition, between the first and second watering, a step of incubating, in a suitable medium, said ΔMAT helper strain and the conidia of a first *T. reesei* strain of a first mating type.

According to one embodiment, said first watering, and optionally the step of incubating, in a suitable medium, said ΔMAT helper strain and the conidia of a first *T. reesei* strain of a first mating type, lasts at least 2 days, preferably between 2 and 7 days, and in particular at least 3 or 4 days. Preferentially, according to this embodiment, said first watering, and optionally the step of incubating, in a suitable medium, said ΔMAT helper strain and the conidia of a first *T. reesei* strain of a first mating type, is carried out in alternating light and darkness, preferably between 3 and 12 hours of light (day) and between 12 and 21 hours of darkness (night).

According to one preferred embodiment of the invention, said incubation, in a suitable medium, of said ΔMAT helper strain and of the conidia of a first *T. reesei* strain of a first mating type is an alternating day/night incubation. Preferentially, the day/night alternating is an alternating of 12 hours of light and hours of darkness. This is the most favorable condition for sexual reproduction (Seidl, V., et al. (2009)).

According to one preferred embodiment of the invention, said incubation, in a suitable medium, of said ΔMAT helper strain and of the conidia of a first *T. reesei* strain of a first mating type lasts 5 to 7 days, preferably 7 days.

According to one preferred embodiment of the invention, said incubation, in a suitable medium, of said ΔMAT helper strain and of the conidia of a first *T. reesei* strain of a first mating type is carried out at an ambient temperature, in particular at 24° C.

According to one preferred embodiment of the invention, said method for restoring sexual reproduction between two sterile female strains of *T. reesei* comprises, in addition, a step of obtaining stromata. According to the invention, the term "stromata" is understood to mean the macroscopic structures (having a diameter of 3-4 mm to 2 cm) which result from sexual reproduction. These structures consist of tissues of maternal origin (the tissues forming them come from the helper strain acting as a female) and are surface-pigmented (brown color).

According to one preferred embodiment of the invention, said method for restoring sexual reproduction between two sterile female strains of *T. reesei* comprises, in addition, after the second watering, a step of incubating, in a suitable medium, the ΔMAT helper strain, the conidia of a first *T. reesei* strain of a first mating type and the conidia of a second *T. reesei* strain of a second mating type, in particular until the stromata appear, and more particularly until the pigmented stromata are visible to the naked eye.

According to one embodiment, said second watering, and optionally the step of incubating, in a suitable medium, the ΔMAT helper strain, the conidia of a first *T. reesei* strain of a first mating type and the conidia of a second *T. reesei* strain of a second mating type, lasts as least 5 days, preferably between 5 and 15 days. Preferentially, according to this embodiment, said second watering, and optionally the step of incubating, in a suitable medium, the ΔMAT helper strain, the conidia of a first *T. reesei* strain of a first mating type and the conidia of a second *T. reesei* strain of a second mating type, is carried out in alternating light and darkness, preferably between 3 to 12 hours of light (day) and between 12 and 21 hours of darkness (night).

According to one preferred embodiment of the invention, said incubation, in a suitable medium, of said ΔMAT helper strain, of the conidia of a first *T. reesei* strain of a first mating type and of the conidia of a second *T. reesei* strain of a second mating type is an alternating day/night incubation. Preferentially, the alternating day/night is an alternating of 12 hours of light and 12 hours of darkness.

According to one preferred embodiment of the invention, said incubation, in a suitable medium, of said ΔMAT helper strain, of the conidia of a first *T. reesei* strain of a first mating type and of the conidia of a second *T. reesei* strain of a second mating type is carried out at an ambient temperature, in particular at 24° C.

According to one embodiment of the invention, said method comprises, in addition, after the stromata have appeared, a step of amplifying said stromata. Said amplifying step is carried out by performing at least one transfer of the stromata obtained into a new suitable medium (for example PDA). The new suitable medium may be the same as that previously used, or a different suitable medium. The transfer of the stromata into a new suitable medium (for example into a new petri dish comprising a suitable medium) makes it possible to very significantly and unexpectedly multiply the final number of stromata obtained (example 4). According to this aspect of the invention, several successive subculturings can be performed, which means that several transfers of the previously obtained stromata can be transferred several times into a new suitable medium (for example, 1, 2, 3, 4, 5 or 6 transfers of stromata can be performed). According to one embodiment, said amplifying step lasts at least 3 days, for example from 3 to 21 days, preferably from 5 to 15 days, and is preferably carried out in alternating light/darkness, in particular between 3 and 12 hours of light (day) and between 12 and 21 hours of darkness (night), more particularly 12 hours of light and 12 hours of darkness. The amplifying step (i.e. the transfer of the stromata into a new suitable medium) makes it possible (1) to quantitatively increase the number of stromata, by at least 20% and even by at least 50% compared with a process without an amplifying step, but also (2) to increase the maturity of the stromata.

According to one particularly preferred embodiment of the invention, said method is a method for restoring sexual reproduction between two sterile female strains of *T. reesei*, comprising the following steps:

incubation, in particular in the dark, in a suitable medium, of a ΔMAT helper strain, said strain being a fertile female strain of *T. reesei* wherein the locus of the MAT mating type has been knocked out, a first watering of said ΔMAT helper strain with conidia of a MAT1-1 first sterile female strain, a step of incubating, in particular in alternating day/night, said ΔMAT helper strain and the conidia of the MAT1-1 first sterile female strain, a second watering of said ΔMAT helper strain and of the conidia of the MAT1-1 first sterile female strain, with conidia of a MAT1-2 second sterile female strain, a step of incubating, in particular in alternating day/night, said ΔMAT helper strain and the conidia of the MAT1-1 first sterile female strain, with conidia of the MAT1-2 sterile female strain, in particular until the stromata appear, optionally a step of amplifying the stromata.

According to one particularly preferred embodiment of the invention, said method is a method for restoring sexual reproduction between two sterile female strains of *T. reesei*, comprising the following steps:

incubation, in particular in the dark, in a suitable medium, of a ΔMAT helper strain, said strain being a fertile female strain of *T. reesei* wherein the locus of the MAT mating type has been knocked out, a first watering of said ΔMAT helper strain with conidia of a MAT1-1 first QM6a strain or of a MAT1-1 sterile female strain, a step of incubating, in particular in an alternating day/night, said ΔMAT helper strain and the conidia of the MAT1-1 QM6a strain or of a MAT1-1 sterile female strain, a second watering of said ΔMAT helper strain and of the conidia of the MAT1-1 QM6a strain, or of a MAT1-1 sterile female strain, with conidia of a MAT1-2 second QM6a strain or of a strain derived from the MAT1-2 QM6a strain or of a MAT1-2 sterile female strain, a step of incubating, in particular in alternating day/night, said ΔMAT helper strain and the conidia of the MAT1-1 QM6a strain, or of a MAT1-1 sterile female strain, with conidia of the MAT1-2 QM6a strain or of a strain derived from the MAT1-2 QM6a strain or of a MAT1-2 sterile female strain, in particular until the stromata appear, optionally a step of amplifying the stromata.

According to one preferred embodiment of the invention, said restoring method also comprises obtaining a *T. reesei* strain. The obtaining of this new *T. reesei* strain, derived from sterile female strains of *T. reesei*, means that the restoring of sexual reproduction between two sterile female strains of *T. reesei* has indeed been restored according to the method of the invention.

In a second aspect, the invention thus relates to the use of a *T. reesei* strain obtained by means of the method mentioned above, for producing cellulases or biofuel.

The invention will now be illustrated by the examples and the Figures that follow. The examples below aim to cast light on the subject of the invention and to illustrate advantageous embodiments, but in no way aim to restrict the scope of the invention.

FIGURES

FIG. 1 represents the principle of sexual reproduction in the filamentous fungus *T. reesei*.

FIG. 2 represents sexual reproduction in *T. reesei*. Part (A) represents sexual reproduction between two natural isolates (A) and part (B) represents sexual reproduction between two QM6a strains.

FIG. 3 represents the principle of the method of the helper strain.

FIG. 4 represents the protocol for implementing the method of the helper strain according to the present invention.

FIG. 5 represents the stromata obtained following the implementation of the method of the helper strain according to the present invention.

FIG. 6 represents the final assembly of the knockout cassette in the pUC19 plasmid (plasmid used to obtain the ΔMAT helper strain according to the present invention). The lines correspond to the primers which are not positioned to scale. The numbers correspond to the primers: 1=5'mat1-2-F; 2=5'mat1-2-R; 3=mat1-2/Hph-F; 4=mat1-2/Hph-R; 5=3'mat1-2-F; 6=3'mat1-2-R; 7=K7 Del Mat1-2-F and 8=K7-Del-Mat1-2-R.

FIG. 7 represents the position of the primers chosen for the amplification of the various fragments of the knockout cassette. The number "(1)" represents the "5'flank+marker" fragment, and the number "(2)" represents the "marker+3'flank" fragment.

FIG. 8 represents the amplification of stromata. The stromata obtained following the implementation of the method of the helper strain according to the present invention (such as those obtained in FIG. 5) are presented in the petri dishes A1 and B1. The stromata are transferred onto a PDA medium (this corresponds to the petri dishes A2 and B2) and the number of stromata can thus be multiplied. This amplification/multiplication step can thus be repeated several times, by transferring the stromata obtained onto a new PDA medium (this corresponds to the petri dishes A3 and B3).

EXAMPLES

Example 1: Materials & Methods

The present invention uses three different strains. The three strains that were used in the examples are the following:

the two sterile strains to be crossed: the QM6a MAT1-1 strain and the QM6a MAT1-2 strain. To obtain the QM6a MAT1-1 strain, the MAT1-2 locus was replaced with the MAT1-1 locus in the QM6a MAT1-2 strain. The QM6a MAT1-2 strain was obtained from the ATCC (reference ATCC® 13631). It is the natural isolate from which all the industrial strains originate.

the ΔMAT helper strain which is a strain wherein the MAT mating type locus has been knocked out. This strain can be constructed according to the protocol indicated below:

Construction of the ΔMAT Helper Strain

This strain must be constructed from a fertile female strain which can cross with the two sterile strains to be crossed before the genetic manipulation.

To construct the MAT1-2 locus knockout cassette, the hygromycin B resistance gene and the 5' and 3' sequences of the MAT1-2 locus were assembled in a plasmid pUC19 (FIG. 6) by means of the Gibson Assembly Kit (New England Biolabs) according to the producer's recommendations. The hygromycin B resistance gene was used as a selectable marker in the present invention, but another selectable marker may absolutely be used.

The pUC19 recipient plasmid was digested beforehand with the XbaI and EcoRI enzymes. The sequences of approximately 1000 bp upstream and downstream of the MAT1-2 locus were amplified using the 5'mat1-2-F and 5'mat1-2-R primers for the upstream region and the 3'mat1-2-F and 3'mat1-2-R primers for the downstream region (Table 1). These primers contain homology regions which allow recombination with pUC19 on one side and the hygromycin resistance gene on the other. The hygromycin B resistance gene was amplified from the pUT1140 plasmid by means of the mat1-2/Hph-F and mat1-2/Hph-R primers. These primers contain homology regions which allow recombination with the MAT1-2 locus on one side and pUC19 on the other.

Secondly, the knockout cassette was amplified from the bacterial DNA by means of the K7-Del-Mat1-2-F and K7-Del-Mat1-2-R primers. The PCR products obtained were purified using the PCR Purification Kit (Qiagen) and were used to transform protoplasts of the B31 fertile wild-type strain using $CaCl_2$ and polyethylene glycol (PEG). A strain other than the B31 strain could have been used, provided that it is fertile female. The sequence of the plasmid used to transform the B31 strains is represented by SEQ ID No.: 17.

The B31 strain (MAT1-2 mating type) is a descendant of the *T. reesei* strain CBS999.97 (ATCC® 204423) (Sexually Competent, Sucrose- and Nitrate-Assimilating Strains of *Hypocrea jecorina* (*Trichoderma reesei*) from South American Soils). It is the equivalent of the MAT1-2 strain CBS999.97 of the article by Seidl et al. (2009).

The transformants were stabilized and regenerated on a PDA medium containing 0.8 M of sucrose and 100 μg/ml of hygromycin B. The colonies were then subcultured and were purified by isolation of the conidia on the PDA-hygromycin selection medium. They were then subjected to phenotypic screening which consists in crossing the B31 transformants with the A2 natural isolate which is of MAT1-1 mating type and which is compatible with the B31 strain: if the MAT locus has indeed been knocked out, then there will be no sexual reproduction and thus an absence of stromata.

A PCR amplification then makes it possible to verify that the native gene has indeed been replaced with the knockout cassette. This validation is carried out in two steps. The first consists in verifying the knockout of the gene by performing a PCR with the primers for amplifying the gene (Mat1-2-F internal and Mat1-2-R internal) (FIG. 7). If said gene is indeed knocked out, no amplification should be obtained. However, in order to verify that this result is indeed a consequence of the absence of the gene and not of a poor operation of the PCR, a control pair of primers (EF1 and EF2), making it possible to amplify an internal fragment of 880 bp of the tef1 gene (encoding the a1 translation elongation factor) present in the genome of all the *T. reesei* strains, is also used. In a second step, the amplification of the "5'flank+marker" and "marker+3'flank" fragments is carried out in order to verify the presence of the knockout cassette at the locus. The position of the primers chosen is presented in FIG. 7. In order to validate the insertion of the genetic cassette at the site, the primers must be chosen downstream of the 5'flank fragment and upstream of the 3'flank fragment (primers Dmat1-2verif5F associated with verifHygro5' and Dmat1-2verif3R associated with verifHygro3').

The sequences of the primers used in the present invention are indicated in Table 1 below.

TABLE 1

Summaries of the primers used for the knockout and replacement of the MAT locus

| Primer name | Primer sequence (5' → 3') |
| --- | --- |
| 5'mat1-2-F | TGCATGCCTGCAGGTCGACTCTAGACCCTTCCTGACCCTGGACTG (SEQ ID NO: 1) |
| 5'mat1-2-R | GGTACACTTGGACTGCGTTGACTGATGGTG (SEQ ID NO: 2) |
| mat1-2/Hph-F | CAACGCAGTCCAAGTGTACCTGTGCATTCTG (SEQ ID NO: 3) |
| mat1-2/Hph-R | CCTTGCCAAGGCAGTGCTAGTGTGTGTAC (SEQ ID NO: 4) |
| 3'mat1-2-F | TAGCACTGCCTTGGCAAAGGCTAGACACTAC (SEQ ID NO: 5) |
| 3'mat1-2-R | TTGTAAAACGACGGCCAGTGAATTCATGTACAATTACCACATGCG (SEQ ID NO: 6) |
| K7-Del-Mat1-2-F | CCAGGGCTTTGAGAGCAGTA (SEQ ID NO: 7) |
| K7-Del-Mat1-2-R | CTGGTGGCTGACACTTGCTA (SEQ ID NO: 8) |
| Dmat1-2verif5F | GTACTGGTTGTTGGGCTGTG (SEQ ID NO: 9) |
| Dmat1-2verif3R | CGGAGCAACTCTCAGGAAAC (SEQ ID NO: 10) |
| verifHygro5' | CTCCGTAACACCCAATACGC (SEQ ID NO: 11) |
| verifHygro3' | CTCTGGGCAAAGCACCAATC (SEQ ID NO: 12) |
| MAT1-2-F internal | TTCAGTGTTGGCCATTTTGA (SEQ ID NO: 13) |
| MAT1-2-R internal | GCTTCTCAAGCAAGGCAAGT (SEQ ID NO: 14) |
| EF1 | ATGGGTAAGGAGGACAAGAC (SEQ ID NO: 15) |
| EF2 | GGAAGTACCAGTGATCATGTT (SEQ ID NO: 16) |

TABLE 2

Sequence of the plasmid used to transform the B31 strains
Sequence of the plasmid (SEQ ID No.: 17)

tgcagcactggggccagatggtaagccctcccgtatcgtagttatctacacgacggggagtcaggcaactatggatgaacgaaatagacagatcgctgagat
aggtgcctcactgattaagcattggtaactgtcagaccaagtttactcatatatactttagattgatttaaaacttcattttttaatttaaaaggatctaggt
gaagatcctttttgataatctcatgaccaaaatcccttaacgtgagttttcgttccactgagcgtcagacccgtagaaaagatcaaaggatcttcttgaga
tcctttttttctgcgcgtaatctgctgcttgcaaacaaaaaaaccaccgctaccagcggtggtttgtttgccggatcaagagctaccaactctttttccgaa
ggtaactggcttcagcagagcgcagataccaaatactgttcttctagtgtagccgtagttaggccaccacttcaagaactctgtagcaccgcctacatacct
cgctctgctaatcctgttaccagtggctgctgccagtggcgataagtcgtgtcttaccgggttggactcaagacgatagttaccggataaggcgcagcggtc
gggctgaacggggggttcgtgcacacagcccagcttggagcgaacgacctacaccgaactgagatacctacagcgtgagctatgagaaagcgccacgcttcc
cgaagggagaaaggcggacaggtatccggtaagcggcagggtcggaacaggagagcgcacgagggagcttccaggggaaacgcctggtatctttatagtcc
tgtcgggtttcgccacctctgacttgagcgtcgatttttgtgatgctcgtcaggggcggagcctatggaaaaacgccagcaacgcggcctttttacggtt
cctggccttttgctggccttttgctcacatgttctttcctgcgttatcccctgattctgtggataaccgtattaccgcctttgagtgagctgataccgctcg
ccgcagccgaacgaccgagcgcagcgagtcagtgagcgaggaagcggaagagcgcccaatacgcaaaccgcctctccccgcgcgttggccgattcattaatg
cagctggcacgacaggtttcccgactggaaagcgggcagtgagcgcaacgcaattaatgtgagttagctcactcattaggcaccccaggctttacactttat
gcttccggctcgtatgttgtgtggaattgtgagcggataacaatttcacacaggaaacagctatgaccatgattacgccaagcttgcatgcctgcaggtcga
ctctagaccttcctgaccctggactgtccagtggccaccggggcgtggctccagggctttgagagcagtaattggtgggagtttggtagttgacatggctg
cgaaaattggtgtccttcagaagttggtcaaggttgattattgaatcagtttgcttcgagtggtgatgaagaaatccccagagtatgagggtatgggatcag
tgggatgttgaaggtgagaataacaggtctgcgaaggggccgccgagtccgtgtggggtcttcttcaggttgctaaggttctactctctgcaagtgaaataa
aagtgaaggatcgaggtgaatggacgcttgtgcccatgagttcacctcacttttaactcactctgctgcatctgagaccctgcagaagtaaggcgaaagctt
gtcagtgggaaaagacccacggcaccatttaaatgtttacgtatgtggatatccgctaaatacgcctgctgtttgtgttggctcttgccaagatcaatttca
gcttctgccagtatttcaagtcaaacgttgtcatgaactacctccatgttgaaattcttcatggatcgtacactgtccgtttggaatctcagatctgaatcg
tatgaaataacagaatcgagctttcgcaactagatgtcccagcaacattgcgcccctggaaagtgataaactgcaactgcatttgtgtgaaaccattggcat
aagtgattgcgctctctggcggaacggacgaagacatgttgcttgatcttatcctttccatggagatcgtatatattctgatttgatgcaaatggtatgtac
ataaatgtccttcacgaactttcaggttgttcccaaagctaaacttcacgcgcatcttgggtgaagtactgcctcgaacgtcatgcacacctggagagcatt
ttgctggtgtgcgaaatgaggatatctccacggtgggcgtattgttacgaagatgcacaccctctggcgatgggcggtgggactgctagattctagcccca
acacttcctttagaaggtacctaggtacgcttgcaaggttccttaggaggtagcttgtcgttggcaagcagaaatacatattacctagtagtacctaggttt
ctaccttaccttcttacatatcagtagtacctagtcattttccccaaggagggagggtgagaaaagagagataggtggggagcgcgcactgacctggcgct
aaataacggaggggctggggggcactattcagattcactcgctttgggttggcagctctcatcaataaaggccagtaagttgaatcaccacggcacgttcc
ggctcacttgtagctcaccctccacccacagccttttcaattcttcaaagcattacctaggcgaccgaaaacttcctacctctcaagttcctcctatcttcc
aactcctgcatcaacgttcatatcccatcttctcgcgatatattaccagagcaagcccgcaccatcagtcaacgcagtccaagtgtacctgtgcattctggg
taaacgactcataggagagttgtaaaaaagtttcggccggcgtattgggtgttacggagcattcactaggcaaccatgcatccttactattgtataccatct
tagtaggaatgatttcgaggtttatacctacgatgaatgtgtgtcctgtaggcttgagagttcaaggaagaaacatgcaattatctttgcgaacccagggct
ggtgacggaattttcatagtcaagctatcagagtaaagaagaggagcatgtcaaagtacaattagagacaaatatatagtcgcgtggagccaagagcggatt
cctcagtctcgtaggtctcttgacgaccgttgatctgcttgatctcgtctcccgaaaatgaaaatagctctgctaagctattcttctcttcgccggagcctg
aaggcgttactaggttgcagtcaatgcattaatgcattgcagatgagctgtatctggaagagggtaaacccgaaaacgcgttttattcttgttgacatggagc
tattaaatcactagaaggcactctttgctgcttggacaaatgaacgtatcttatcgagatcctgaacaccatttgtctcaactccggctagcgaattctcga
ctcattcctttgccctcggacgagtgctggggcgtcggtttccactatcggcgagtacttctacacagccatcggtccagacggccgcgcttctgcgggcga
tttgtgtacgcccgacagtcccggctccggatcggacgattgcgtcgcatcgaccctgcgcccaagctgcatcatcgaaattgccgtcaaccaagctctgat
agagttggtcaagaccaatgcggagcatatacgcccggagtcgtggcgatcctgcaagctccggatgcctccgctcgaagtagcgcgtctgctgctccatac
aagccaaccacggcctccagaagaagatgttggcgacctcgtattgggaatcccgaacatcgcctcgtccagtcaatgaccgctgttatgcggccattgt
ccgtcaggacattgttggagccgaaatccgcgtgcacgaggtgccggacttcggggcagtcctcggcccaaagcatcagctcatcgagagcctgcgcgacgg TABLE 2-continued

| Sequence of the plasmid used to transform the B31 strains<br>Sequence of the plasmid (SEQ ID No.: 17) |
|---|
| acgcactgacggtgtcgtccatcacagtttgccagtgatacacatggggatcagcaatcgcgcatatgaaatcacgccatgtagtgtattgaccgattcctt |
| gcggtccgaatgggccgaacccgctcgtctggctaagatcggccgcagcgatcgcatccatagcctccgcgaccggttgtagaacagcgggcagttcggttt |
| caggcaggtcttgcaacgtgacaccctgtgcacggcgggagatgcaataggtcaggctctcgctaaactccccaatgtcaagcacttccggaatcgggagcg |
| cggccgatgcaaagtgccgataaacataacgatctttgtagaaaccatcggcgcagctatttacccgcaggacatatccacgccctcctacatcgaagctga |
| aagcacgagattcttcgccctccgagagctgcatcaggtcggagacgctgtcgaacttttcgatcagaaacttctcgacagacgtcgcggtgagttcaggct |
| ttttcatgatggccctcctaccggtgatctcagctgtaggaaagagaagaaggttagtagtcgacatggtggccctcctatagtgagtcgtattatactatg |
| ccgatatactatgccgatgattaattgtcaacactaggcgccggtcacaactagtagatatcacttacgtgttgagaggcggcatgcgataagaggtgtaat |
| tacctgagaacatcttgttgccctgctttccgtgcgaaatactaccggtactttgggaaacaagggaacaggagggcgctgctgtgcgcggttctgagtgt |
| tcaggattgaagctgaagaaggtgctgaggaagcgtagaactgttgcggacgcgagttctgagaagagctgtaccgattggtgaaagccgaagaagtgagtt |
| ggtgccctgttgcctggataatgtttgcaactcgctggttctgcagagacggagacaaatgctggctacgatgttgctgattcaggttgatacctcggtcga |
| gacactgttttggtttgatagggtggatttggttgcagagaagagaaaggaaggtcaaagagggaaaactgggcggagggaaggattttgtatcaggcagca |
| aactgccactgcagtggccctggcagtgccgggcgaggcacccacgcacggccgcgcaaccggttggtccttgcccaccacgaaacccttctgaaaggtcag |
| atggaagtgtgcgacagtgcgcgtccccaagccaatgcaggcgccatgcactccccacccgcaagattcactgtgcgttcttattggttgccgcaaggccag |
| ccaaagggggaagtatgagtcacagcaccgatacaagaaaattgcagaactaacatatggatgcgcgcgctattctgtagagctctgggcaaagcaccaatc |
| ctgcgggtcggtacacacactagcactgccttggcaaaggctagacactacggaaatctcgcttcggtccttatagattctgtgagatattgtcgcttgtgc |
| caatggtaaggccgaaatgatgcttttaatggaacagctcatctaacaggccacagatgatttcatagctaggctgaatgcctcgggcagtttcgggcatgg |
| tacaaacagagtaccacgtccctaaaacaggcggaactttcaccgctcagtttcctcgacagctttcagaggtttgtaagtgcaccttgctatctatttctc |
| tggacggcacagtaactgatcattgttacatgaacagtagttcttgccttggtggacgaggaaacagaccacttcataggaaatctttttggaacgacctgc |
| agagatgtgcaactacacaccgagttacccagactacaagttcagggccatggagccttgggcggagactacctaatatcagagagcaagctgtggctgcct |
| ctacaccgggtcaagcattggaatcaggctgtgtttttcaagtagcgagagctttggttgtaatagggttccatcagcatactatgccgattgcctagtagg |
| cactcataaccgtggcaaccaagccggacacaggtccttctagatcacagttccatattcttcgagatgataaattaaagtcaaatgctaccatctacaacc |
| tcaatctgcaactttgcttctttcacactagacctctcgcctcccgtcactctgccaatgatgaacactagcatctcgtatatcgtgaaaggtttagctacc |
| ctcaaacttgagttgtggagatcaactgatctcgttcggactacattgcggcgacaacttgaattggacacgataaggaaaaggccaaactttgtgaggtgc |
| tgagggcagtaagcacgacagtctaaagagaaagaaatgccgcgttcactacagccatttgaggtctaacaacaagctgattcaactgcaacaggcgctatg |
| tcaagaaggtgatccgttccaatcgctgctccaaatgaaagtaccgcaccgccactcagagcctcgttctttctcgccggagggacctagcggccgggcgca |
| gatatagaacgaccttcctgttagcaagtgtcagccaccagctggtctgcgcatgtggtaattgtacatgaattcactggccgtcgttttacaacgtcgtga |
| ctgggaaaaccctggcgttacccaacttaatcgccttgcagcacatccccctttcgccagctggcgtaatagcgaagaggcccgcaccgatcgcccttccca |
| acagttgcgcagcctgaatggcgaatggcgcctgatgcggttttctccttacgcatctgtgcggtatttcacaccgcatatggtgcactcagtacaatctgc |
| tctgatgccgcatagttaagccagccccgacacccgccaacacccgctgacgcgccctgacgggcttgtctgctcccggcatccgcttacagacaagctgtg |
| accgtctccgggagctgcatgtgtcagaggttttcaccgtcatcaccgaaacgcgcgagacgaaagggcctcgtgatacgcctatttttataggttaatgtc |
| atgataataatggtttcttagacgtcaggtggcacttttcggggaaatgtgcgcggaacccctatttgtttatttttctaaatacattcaaatatgtatccg |
| ctcatgagacaataaccctgataaatgcttcaataatattgaaaaaggaagagtatgagtattcaacatttccgtgtcgcccttattcccttttttgcggca |
| ttttgccttcctgtttttgctcacccagaaacgctggtgaaagtaaaagatgctgaagatcagttgggtgcacgagtgggttacatcgaactggatctcaac |
| agcggtaagatccttgagagttttcgccccgaagaacgttttccaatgatgagcacttttaaagttctgctatgtggcgcggtattatcccgtattgacgcc |
| gggcaagagcaactcggtcgccgcatacactattctcagaatgacttggttgagtactcaccagtcacagaaaagcatcttacggatggcatgacagtaaga |
| gaattatgcagtgctgccataaccatgagtgataacactgcggccaacttacttctgacaacgatcggaggaccgaaggagctaaccgcttttttgcacaac |

TABLE 2-continued

Sequence of the plasmid used to transform the B31 strains
Sequence of the plasmid (SEQ ID No.: 17)

atgggggatcatgtaactcgccttgatcgttgggaaccggagctgaatgaagccataccaaacgacgagcgtgacaccacgatgcctgtagcaatggcaaca acgttgcgcaaactattaactggcgaactacttactctagcttcccggcaacaattaatagactggatggaggcggataaagttgcaggaccacttctgcgc tcggcccttccggctggctggtttattgctgataaatctggagccggtgagcgtgggtctcgcggtatcat Following these phenotypic and molecular verifications, the B31::ΔMAT-hph helper strain was obtained. It is a ΔMAT helper strain (a strain of *T. reesei* wherein the locus of the MAT mating type has been knocked out) according to the present invention.

Example 2: Comparative Examples with Various Methods Aiming to Restore Sexual Reproduction Between Two QM6a Industrial Strains of *T. Reesei*

All the tests were carried out in Petri dishes containing PDA medium. This is the most optimal medium for sexual reproduction of *T. reesei*.

a/ Method 1: Production of a Trikaryon

This is the same method as that described in P. anserina (Jamet-Vierny, C., Debuchy, R., Prigent, M. & Silar, P. (2007). IDC1, a pezizomycotina-specific gene that belongs to the PaMpk1 MAP kinase transduction cascade of the filamentous fungus *Podospora* anserina. *Fungal genetics and biology FG & B* 44, 1219-1230).

In order to obtain a trikaryon, the strains were incubated separately for two days at most at 30° C. in order to prevent the formation of conidia and to obtain only mycelium. After two days of growth, an agar implant 0.5 cm by 0.5 cm of each of the strains involved (three for a trikaryon) was cut out and placed in a 2 ml Eppendorf tube containing 500 µl of sterile water. The mycelia were mixed by means of a FastPrep®-24 (MP Biomedicals) for 20 seconds at a speed of 4 m/s, and 10 µl of the ground material were deposited on the Petri dishes. The dishes were incubated in an incubator at 24° C. with alternating 12 hours of light and 12 hours of darkness.

The experiment was carried out a first time in triplicate. No stromata were obtained. The dishes were kept in the incubator until the medium dried, that is to say approximately one month.

Since the obtaining of trikaryon is a rare event, the experiment was repeated and 10 different Petri dishes were inoculated. No stromata were obtained.

b/ Method 2: Production of a Trikaryon

This method is identical to method 1, but differs by virtue of its incubation. In this case, the Petri dishes are not placed in an incubator where it is 24° C. or where there are 12 hours of light and 12 hours of darkness, but are left on the workbench in the laboratory in which the temperature is not constant (daily variation) and where there is no luminosity control (natural luminosity). The mixture of the three strains was inoculated onto ten different Petri dishes. No stromata were obtained.

c/ Method 3: Confrontation of the Three Strains

The three strains were inoculated onto a Petri dish at equal distance from one another and at a maximum distance from the center of the Petri dish. The dish was incubated at 24° C. with alternating day/night (12 hours of light and 12 hours of darkness). No stromata were obtained.

d/ Method 4: Mixture of the Three Strains at the Center of the Petri Dish

The three strains were inoculated in isolation onto a sheet of cellophane placed on the Petri dish. After 2-3 days of growth in the dark, the mycelia were removed, ground using balls in a FastPrep®, mixed in a 1:1:1 ratio and then deposited at the center of the Petri dish with various concentrations (1, 1/10, 1/100, 1/1000). No stromata were obtained.

e/ Method 5: Isolated Inoculation of the Three Strains

The three strains were inoculated in isolation onto a sheet of cellophane placed on a Petri dish. After 2-3 days of growth in the dark, the mycelia were removed, ground using balls in a FastPrep, then mixed in a 1:1:1 ratio. This mixture was inoculated into a PD (Potato Dextrose Broth) liquid medium supplemented with 1% of $KH_2PO_3$ and incubated (with or without shaking) for one to two days and was then deposited at the center of a Petri dish with various concentrations (1, 1/10), with or without addition of 5 mM of ascorbic acid. No stromata were obtained.

f/ Method 6: Inoculation of the Three Strains

The three strains were inoculated together from conidia into a PD (Potato Dextrose Broth) liquid medium supplemented with 1% of $KH_2PO_3$, and incubated (with or without shaking) for 1 to 2 days and were then deposited at the center of a dish of PDA with various concentrations (1, 1/10), with or without addition of 5 mM of ascorbic acid. No stromata were obtained.

g/ Method 7: Isolated Inoculation of the Three Strains

The three strains were inoculated in isolation onto a sheet of cellophane placed on a Petri dish. After 2-3 days of growth in the dark, the mycelia were removed, ground using balls in a FastPrep, then mixed with a 1:1:1 ratio (QM6a 1-1:QM6a 1-2:ΔMAT), or 1:1:2 or 1:1:5. The mixture was (i) either plated out over the entire dish, (ii) or inoculated at the center of the dish with various dilutions (1, 1/10 and 1/100) on PDA medium, with or without addition of 5 mM of ascorbic acid. The dishes were then incubated at 24° C., (i) either in alternating day/night, (ii) or for an incubation of one night in the dark then alternating day/night, (iii) or in the dark for three days followed by alternating day/night, (iv) or in the dark from 15 days followed by alternating day/night. No stromata were obtained.

h/ Method 8: Sequential Watering with Addition of Cellular Extracts

Fertile wild-type isolates of *T. reesei* strains were placed in confrontation on a sheet of cellophane deposited on PDA. The biological material of these crosses was recovered from T=0 to T=96h after inoculation and was subjected to protein extraction. The protein extracts were sterilized by filtration. Finally, the watering method was applied and the various cell extracts obtained were added to the conidia. A first watering with the MAT1-1 conidia, then a second watering with the MAT1-2 conidia (or vice versa) were carried out. No stromata were obtained.

i/ Method 9: Sequential Watering According to the Invention

Obtaining Conidia:

Four to six days before the watering, Petri dishes are inoculated with each of the conidia donor strains (MAT1-1 then MAT1-2) which will serve for the watering of the helper strain, and incubated at 30° C. in the light in order for there to be production of conidia.

On the day of the watering, 4 ml of sterile water is deposited on the donor strain (MAT1-1 or MAT1-2) and the conidia are harvested. The conidia are counted and their concentration is adjusted to between $10^6$ and $10^8$ conidia/ml.

Watering:

In the watering technique, the ΔMAT helper strain has the function of a female strain that will provide the maternal tissues required for the production of the stromata. The helper strain will be successively watered by the MAT1-1 then MAT1-2 conidia.

The ΔMAT helper strain is watered uniformly with 1 ml of conidia of the first mating type, then incubated for 7 days, watered with 1 ml of conidia of the second mating type and incubated until stromata are obtained.

The ΔMAT helper strain is cultured on a PDA medium and incubated at 24° C. for 4 days and in the dark. After 4 days in incubation, the helper strain was watered with 1 ml of conidia of MAT1-1 mating type and incubated at 24° C. for 7 days with alternating light for 12 h and darkness for 12 h.

Finally, the helper strain was watered with 1 ml of MAT1-2 conidia and incubated at 24° C. with alternating light for 12 h and darkness for 12 h until the stromata appeared. This method made it possible to obtain stromata.

Six different experiments (exp 1 to exp 6) were carried out. The latter differ by virtue of the preincubation time (4, 5 or 6 days) and by virtue of the number of conidia that were watered. The results are presented in Table 3 below.

TABLE 3

Total number of stromata obtained with the 6 dishes

| Watering | Exp 1 = pre-incubation 4 d | Exp 2 = pre-incubation 5 d | Exp 3 = pre-incubation 6 d | Exp 4 = pre-incubation 4 d | Exp 5 = pre-incubation 5 d | Exp 6 = pre-incubation 6 d |
|---|---|---|---|---|---|---|
| $10^6$ | 1 | 3 | 1 | 0 | 0 | 0 |
| $10^7$ | 53 | 46 | 37 | 1 | Many pigmented structures* | 0 |
| $10^8$ | 61 | 71 | 28 | 1 | 26 | 0 |

*Many pigmented structures which resemble stromata, but which are very small in size (approximately 2 mm), were obtained. There are so many of them that they are stuck to one another, which makes them difficult to count.

The sequential watering technique makes it possible to repeatedly obtain stromata. The optimal conditions for obtaining the stromata are the following:

preincubation of the helper strain: 4 or 5 days;
concentration of conidia: $10^7$ and $10^8$ conidia/ml.

Example 3: Various Conditions for Sequential Watering According to the Invention In this example, and as indicated in Table 4, the helper strain was watered by:

a strain of MAT1-1 mating type, then the same strain of the MAT1-2 mating type, or a strain of MAT1-2 mating type, then the same strain of the MAT1-1 mating type, or water at each of the waterings (negative control).

TABLE 4

Summary of the various conditions tested

|  | Watering 1 | Watering 2 |
|---|---|---|
| ΔMAT helper strain | MAT1-1 | MAT1-2 |
| ΔMAT helper strain | MAT1-2 | MAT1-1 |
| ΔMAT helper strain | $H_2O$ | $H_2O$ |

Between watering 1 and watering 2, there is an incubation for 7 days at 24° C. with alternating of light for 12h and darkness for 12h. The results are presented in Table 5 below.

TABLE 5

Total number of stromata obtained with the 2 dishes

| Watering 1 | Watering 2 | Number of stromata obtained on 2 dishes |
|---|---|---|
| MAT1-1 | MAT1-2 | 40 |
| MAT1-2 | MAT1-1 | 12 |
| $H_2O$ | $H_2O$ | 0 |

A first watering with a strain of MAT1-1 mating type thus favors the obtaining of a large number of stromata, in comparison with a first watering with a strain of MAT1-2 mating type.

Example 4: Amplification of the Stromata

The amplification was carried out under alternating of light for 12 h and darkness for 12 h, for a period of 7 to 21 days: the time elapsed between the first series of photos (A1 or B1) and the second series of photos (A2 or B2) is 15 days. The stromata of the A1/B1 Petri dishes obtained according to the invention (for example such as those obtained in example 2) were transferred into a new suitable medium (in this case PDA). The stromata obtained at the end of this transfer are represented in the A2/B2 Petri dishes. A second transfer into a new suitable medium was then carried out: the stromata of the A2/B2 Petri dishes were transferred into a new suitable medium. The stromata obtained at the end of this transfer are represented in the A3/B3 Petri dishes.

The results of these transfers are represented in FIG. 8.

The analysis of the number of stromata obtained made it possible to conclude that:

1) The amplification step (i.e. the transfer of the stromata into a new suitable medium) makes it possible to quantitatively increase the number of stromata, by at least 20% and even by at least 50% compared with a method without amplification step, 2) The amplification step also makes it possible to increase the maturity of the stromata.

REFERENCES

Jamet-Vierny, C., Debuchy, R., Prigent, M. and Silar, P. (2007). IDC1, a pezizomycotina-specific gene that belongs to the PaMpk1 MAP kinase transduction cascade of the filamentous fungus *Podospora* anserina. Fungal genetics and biology: FG & B 44, 1219-1230.

Kubicek, C., Linke, R., Seiboth, B., Haarmann, T, and Lorenz, P, (2014), Genes/Genetic Elements Associated With Mating Impairment In *Trichoderma reesei* QM6a And Its Derivatives And Process For Their Identification (WO2014/102241).

Linke, R., Thallinger, G. G., Haarmann, T., Eidner, J., Schreiter, M., Lorenz, P., Seiboth, B., and Kubicek, C. P. Restoration of female fertility in *Trichoderma reesei* QM6a provides the basis for inbreeding in this industrial cellulase producing fungus. Biotechnology for biofuels 8, 155.

Seidl, V., Seibel, C., Kubicek, C. P. and Schmoll, M. (2009). Sexual development in the industrial workhorse *Trichoderma reesei*. Proceedings of the National Academy of Sciences of the United States of America 106, 13909-13914.

Silar, P. (2014). Simple Genetic Tools to study fruiting body development in Fungi. *The Open Mycology Journal*, 8, 148-155); Jamet-Vierny, C., Debuchy, R., Prigent, M. & Silar, P. (2007). IDC1, a pezizomycotina-specific gene that belongs to the PaMpk1 MAP kinase transduction cascade of the filamentous fungus *Podospora* anserina. *Fungal genetics and biology: FG & B* 44, 1219-1230

The invention claimed is:

1. A method for restoring sexual reproduction between two sterile female strains of *Trichoderma reesei*, comprising the following steps:
a) incubation in a suitable medium of a ΔMAT helper strain, said strain being a fertile female strain of *Trichoderma reesei* wherein the locus of the MAT mating type has been knocked out,
b) a first watering of said ΔMAT helper strain with conidia of a first sterile female strain of *Trichoderma reesei* of a first mating type,
c) a step of incubating, in a suitable medium, said ΔMAT helper strain resulting from step b),
d) a second watering of said ΔMAT helper strain resulting from step c) with conidia of a second sterile female strain of *Trichoderma reesei* of a second mating type, and
e) a step of incubating, in a suitable medium, said ΔMAT helper strain resulting from step d) until stromata appear.

2. The method for restoring sexual reproduction between two sterile female strains of *Trichoderma reesei* as claimed in claim 1, wherein the first mating type of the first *Trichoderma reesei* strain is MAT1-1.

3. The method for restoring sexual reproduction between two sterile female strains of *Trichoderma reesei* as claimed in claim 1, wherein the second mating type of the second *Trichoderma reesei* strain is MAT1-2.

4. The method for restoring sexual reproduction between two sterile female strains of *Trichoderma reesei* as claimed in claim 1, wherein the *Trichoderma reesei* strain is the QM6a strain or a strain derived from the QM6a strain.

5. The method for restoring sexual reproduction between two sterile female strains of *Trichoderma reesei* as claimed in claim 1, wherein step a) of incubating, in a suitable medium, said ΔMAT helper strain lasts at least 2 days.

6. The method for restoring sexual reproduction between two sterile female strains of *Trichoderma reesei* as claimed in claim 1, wherein step a) of incubating, in a suitable medium, said ΔMAT helper strain is an incubation in the dark.

7. The method for restoring sexual reproduction between two sterile female strains of *Trichoderma reesei* as claimed in claim 1, wherein the conidia of the first *Trichoderma reesei* strain of a first mating type and/or the conidia of the second *Trichoderma reesei* strain of a second mating type are present at a concentration of at least $10^5$ conidia/ml.

8. The method for restoring sexual reproduction between two sterile female strains of *Trichoderma reesei* as claimed in claim 1, wherein step b) lasts at least 2 days.

9. The method for restoring sexual reproduction between two sterile female strains of *Trichoderma reesei* as claimed in claim 1, wherein step b) is carried out in alternating light and darkness.

10. The method for restoring sexual reproduction between two sterile female strains of *Trichoderma reesei* as claimed in claim 1, wherein step d lasts at least 5 days.

11. The method for restoring sexual reproduction between two sterile female strains of *Trichoderma reesei* as claimed in claim 1, wherein step d is carried out in alternating light and darkness.

12. The method for restoring sexual reproduction between two sterile female strains of *Trichoderma reesei* as claimed in claim 1, comprising, in addition, after the stromata have appeared, a step of amplifying the stromata.

13. The method for restoring sexual reproduction between two sterile female strains of *Trichoderma reesei* as claimed in claim 1, comprising, in addition, the obtaining of a *Trichoderma reesei* strain.

14. A method of producing cellulases or biofuel comprising incubating a *Trichoderma reesei* strain obtained by means of the method as claimed in claim 1 and isolating the cellulases or biofuel from the incubation media.

15. The method for restoring sexual reproduction between two sterile female strains of *Trichoderma reesei* as claimed in claim 1, wherein step b) and the step of incubating, in a suitable medium, said ΔMAT helper strain resulting from step b), last at least 2 days.

16. The method for restoring sexual reproduction between two sterile female strains of *Trichoderma reesei* as claimed in claim 1, wherein step b) and the step of incubating, in a suitable medium, said ΔMAT helper strain resulting from step b), are carried out in alternating light and darkness.

17. The method for restoring sexual reproduction between two sterile female strains of *Trichoderma reesei* as claimed in claim 1, wherein step d and the step of incubating, in a suitable medium, the ΔMAT helper strain resulting from step d, last at least 5 days.

18. The method for restoring sexual reproduction between two sterile female strains of *Trichoderma reesei* as claimed in claim 1, wherein step d optionally the step of incubating, in a suitable medium, the ΔMAT helper strain resulting from step d are carried out in alternating light and darkness.

* * * * *